US00RE38994E

(19) United States
(12) Reissued Patent
Pandey et al.

(10) Patent Number: US RE38,994 E
(45) Date of Reissued Patent: Feb. 28, 2006

(54) PYROPHEOPHORBIDES CONJUGATES AND THEIR USE IN PHOTODYNAMIC THERAPY

(75) Inventors: Ravindra K. Pandey, Williamsville, NY (US); Thomas J. Dougherty, Grand Island, NY (US)

(73) Assignee: Health Research, Inc., Buffalo, NY (US)

(21) Appl. No.: 10/385,378

(22) Filed: Mar. 7, 2003

Related U.S. Patent Documents

Reissue of:
(64) Patent No.: 5,314,905
Issued: May 24, 1994
Appl. No.: 07/973,174
Filed: Nov. 9, 1992

(62) Division of application No. 07/822,409, filed on Jan. 17, 1992, now Pat. No. 5,198,460, which is a continuation-in-part of application No. 07/597,786, filed on Oct. 15, 1990, now Pat. No. 5,093,349, which is a continuation of application No. 07/221,804, filed on Jul. 20, 1988, now Pat. No. 5,002,962.

(51) Int. Cl.
*A61K 31/409* (2006.01)
*C07D 487/22* (2006.01)

(52) U.S. Cl. ..... 514/410; 514/2; 530/391.1; 530/391.3; 530/391.5; 530/391.7; 530/391.9; 450/145

(58) Field of Classification Search ..... 514/2, 514/410; 530/391.1, 391.3, 391.5, 391.7, 530/391.9; 540/145
See application file for complete search history.

(56) References Cited

U.S. PATENT DOCUMENTS

| | | | | |
|---|---|---|---|---|
| 4,649,151 A | | 3/1987 | Dougherty et al. | 514/410 |
| 4,649,191 A | * | 3/1987 | Hruby | |
| 4,823,244 A | | 4/1989 | Alaybayoglu et al. | 362/194 |
| 4,866,168 A | | 9/1989 | Dougherty et al. | 540/145 |
| 4,883,790 A | | 11/1989 | Levy et al. | 540/145 |
| 4,920,143 A | | 4/1990 | Levy et al. | 514/410 |
| 4,932,934 A | | 6/1990 | Dougherty et al. | 604/21 |
| 4,968,715 A | | 11/1990 | Dougherty et al. | 514/410 |
| 5,002,962 A | | 3/1991 | Pandey et al. | 514/410 |
| 5,015,463 A | | 5/1991 | Dougherty et al. | 424/7.1 |
| 5,026,367 A | | 6/1991 | Leckrone et al. | 606/7 |
| 5,028,621 A | | 7/1991 | Dougherty et al. | 514/410 |
| 5,093,349 A | | 3/1992 | Pandey et al. | 514/410 |
| 5,145,863 A | | 9/1992 | Dougherty et al. | 514/410 |

(Continued)

FOREIGN PATENT DOCUMENTS

| | | |
|---|---|---|
| EP | 0175617 | 9/1985 |
| EP | 0220686 B1 | 12/1992 |
| EP | 0161606 B1 | 4/1993 |
| EP | 0423195 B1 | 4/1994 |
| EP | 0425566 B1 | 10/1994 |
| EP | 1110963 A2 | 6/2001 |
| EP | 1146046 A2 | 10/2001 |
| EP | 1164136 A1 | 12/2001 |
| EP | 1238666 A2 | 9/2002 |
| EP | 1256586 A1 | 11/2002 |
| JP | 0335578 | 4/2001 |
| WO | 8401382 | 4/1984 |
| WO | 9000895 | 2/1990 |
| WO | 9012573 | 11/1990 |
| WO | 9313769 | 7/1993 |
| WO | 9532206 | 11/1995 |
| WO | 9732885 | 9/1997 |
| WO | 9967248 | 12/1999 |
| WO | 9967249 | 12/1999 |

OTHER PUBLICATIONS

Bellnier et al., "Murine pharmacokinetics and antitumor efficacy of the photodynamic sensitizer 2–[1–hexyloxyethyl]–2–devinyl pyropheophorbide–a", *J. Photochem. Photobiol. B: Biol.,* 20:55–61 (1993).
Dougherty et al., "Photoradiation Therapy—Clinical and Drug Advances", *Adv. Exp. Med. Biol.,* 160:3–13 (1983).
English language equivalent of Japanese Patent No. 335578, Apr. 12, 2001.
Jurgens, et al., "Reactions of Chloromethyl Methyl Ether with Chlorin Derivatives", *Liebigs Ann. Chem.,* 12:1992–2005 (1979).
Kessel et al., "Chemistry of Hematoporphyrin–derived Photosensitizers", Section i Chemistry and Photochemistry, *Photochem. Photobiol.,* 46(5):563–568 (1987).
Lipson et al., "The Use of a Derivative of Hematoporphyrin in Tumor Detection", *J. Natl. Cancer Inst.,* 26:1–8 (1961).
Pandey et al., "Improved photosensitizers for photodynamic therapy", *SPIE*, 1645:264–273 (1992).
Pandey et al., "Structure/Activity Relationships Among Photosensitizers Related To Pheophorbides And Bacteriopheophorbides", *Biorg. Med. Chem Ltts.,* 2(5):491–496 (1992).
Pandey et al., "Synthesis and photosensitizing activity of a di–porphyrin ether", *Chemical Abstracts,* 109(15):370 125066B (1988).
Scourides et al., "Nature of the Tumor–localizing Components of Hematoporphyrin Derivative", *Cancer Res.,* 47:3439–3445 (1987).

*Primary Examiner*—Richard L. Raymond
(74) *Attorney, Agent, or Firm*—Michael L. Dunn

(57) ABSTRACT

Conjugate are formed by covalently linking a target-specific compound to pyropheophorbide compound which conjugated are injected into a host and accumulate in tumor tissue to a higher degree than surrounding normal tissues. When the pyropheophorbide compound component of the conjugate is exposed to a particular wavelength of light the compound becomes cytotoxic destroying the tumor or diseased tissue without causing irreversible normal tissue damage. The pyropheophorbide compounds have been shown to have a variety of characteristics when used in photodynamic therapy. These characteristics are further improved when the compounds are bound to a target specific component such as a ligand capable of binding to a specific cellular receptor (e.g. growth hormones and growth factors) or an antibody capable of binding to a particular antigen.

20 Claims, 1 Drawing Sheet

U.S. PATENT DOCUMENTS

| | | | | |
|---|---|---|---|---|
| 5,171,741 | A | 12/1992 | Dougherty | 514/185 |
| 5,173,504 | A | 12/1992 | Dougherty | 514/410 |
| 5,190,966 | A | 3/1993 | Dougherty et al. | 514/410 |
| 5,198,460 | A | 3/1993 | Pandey et al. | 514/410 |
| 5,225,433 | A | 7/1993 | Dougherty et al. | 514/410 |
| 5,257,970 | A | 11/1993 | Dougherty | 604/20 |
| 5,314,905 | A | 5/1994 | Pandey et al. | 514/410 |
| 5,459,159 | A | 10/1995 | Pandey et al. | 514/410 |
| 5,498,710 | A | 3/1996 | Pandey et al. | 540/145 |
| 5,506,255 | A | 4/1996 | Smith et al. | 514/410 |
| 5,591,847 | A | 1/1997 | Pandey et al. | 540/472 |
| 5,770,730 | A | 6/1998 | Pandey et al. | 540/472 |
| 5,864,035 | A | 1/1999 | Pandey et al. | 540/472 |
| 5,952,366 | A | 9/1999 | Pandey et al. | 514/410 |
| 6,103,751 | A | 8/2000 | Pandey et al. | 514/410 |
| 6,495,585 | B1 | 12/2002 | Bellnier et al. | 514/410 |
| 6,534,040 | B1 | 3/2003 | Pandey et al. | 424/9.362 |
| 2001/0046983 | A1 | 11/2001 | Pandey et al. | 514/185 |
| 2002/0128303 | A1 | 9/2002 | Bellnier et al. | 514/410 |
| 2002/0198157 | A1 | 12/2002 | Pandey et al. | 514/23 |
| 2003/0053949 | A1 | 3/2003 | Pandey et al. | 424/1.11 |

* cited by examiner

PYROPHEOPHORBIDES CONJUGATES AND THEIR USE IN PHOTODYNAMIC THERAPY

Matter enclosed in heavy brackets [ ] appears in the original patent but forms no part of this reissue specification; matter printed in italics indicates the additions made by reissue.

This application is *a reissue of U.S. patent application Ser. No. 07/973,174, filed Nov. 9, 1992, which issued as U.S. Pat. No. 5,314,905 on May 24, 1994, and is* a division of earlier filed U.S. patent application Ser. No. 07/822,409 filed Jan. 17, 1992, now U.S. Pat. No. 5,198,460, which is a continuation-in-part of U.S. patent application Ser. No. 07/597,786 filed Oct. 15, 1990, now U.S. Pat. No. 5,093,349 issued Mar. 3, 1992, which is a continuation of U.S. patent application Ser. No. 07/221,804 filed Jul. 20, 1988, now U.S. Pat. No. 5,002,962 issued Mar. 26, 1991, all of which are incorporated herein by reference and to which applications we claim priority under 35 USC §120.

FIELD OF THE INVENTION

This invention relates generally to photosensitive therapeutic compounds and photodynamic therapy (PDT). More particularly, the invention relates to pyropheophorbides, formulations that contain such and their use in the treatment of cancer.

BACKGROUND OF THE INVENTION

As described in U.S. Pat. No. 5,002,962, porphyrin related compounds accumulate at higher concentrations in tumor tissue as compared to normal tissue, and that irradiation of these compounds using light of the proper wavelength results in an energized form which, upon decay, results in cytotoxicity. It is believed that excitation of the porphyrin or related material results in the formation of singlet oxygen which is in fact the toxic agent. However, the compounds administered apparently do not degrade in this process.

Literature relating to the use of "hematoporphyrin derivative" (HPD) describes this process utilizing a preparation obtained when hematoporphyrin dichloride is treated using the procedure of Lipson, R. L., et al. J National Cancer Inst (1961) 26:1–8. More recently, it has been shown that if this hematoporphyrin derivative is treated at a suitable pH, aggregation occurs and the active material in the mixture can be prepared in crude form as a size segregated aggregate (see, for example, U.S. Pat. No. 4,649,151, incorporated herein by reference). This preparation is commercially available under the trademark Photofrin.

The preparation marketed as the Photofrin composition is a mixture. The mixture contains porphyrins joined by ether linkages (Dougherty, T. J., et al, Adv Exp Med Bio (1983) 160:3–13), and more recently, Kessel, D., et al Photochem Photobiol (1987) 46:463–568, has shown that ester linked porphyrins are contained in this mixture as well. Scourides, P. A., et al, Cancer Res (1987) 47:3439–3445 have synthesized an oligomeric mixture of ether linked porphyrins starting from hematoporphyrin dimethyl esters. The mixture was active in PDT, but was as complex a mixture as the Photofrin preparation. Dimers of hematoporphyrin joined by ester linkages have also been prepared by Pandey, R. K., et al, Cancer Res (in press) and the dimers prepared were shown to be absent from the mixture in the Photofrin composition as well as inactive in an in vitro assay.

Thus, it is known in the art that some elements of a mixture prepared when HPD is aggregated and segregated into higher molecular weight components are active in photodynamic therapy. Earlier, the present inventors prepared single compound compositions useful in PDT as disclosed in U.S. Pat. No. 5,002,962. The purified and defined compositions disclosed in U.S. Pat. No. 5,002,962 are useful in photodynamic therapy as are compounds and methods disclosed in U.S. Pat. Nos. 4,920,143 and 4,883,790.

SUMMARY OF THE INVENTION

Pyropheophorbide compounds and pharmaceutical compositions containing such compounds can be used in methods of photodynamic therapy. The pyropheophorbides are encompassed by the following general structural formula I or II.

I

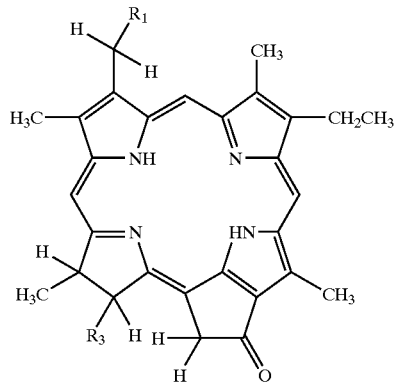

wherein $R_1$ is [$CH_2OR_2$] —$CH_2OR_2$ where $R_2$ is a primary or secondary alkyl containing 1 to 20 carbons; and $R_3$ is [—$CO_2R_4$] —$CH_2CH_2CO_2R_4$ where $R_4$ is H or an alkyl containing 1 to 20 carbons. Other compounds of the invention are encompassed by formula II as follows:

II

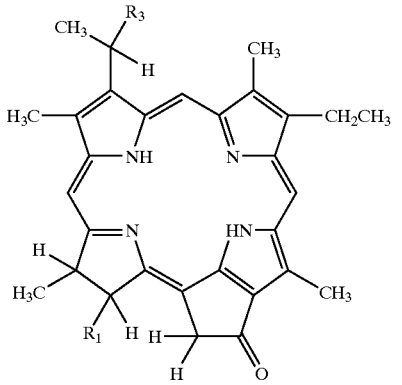

wherein $R_5$ is —$OR_6$ where $R_6$ is a primary or secondary alkyl containing 1 to 20 carbons and $R_7$ is [—$CO_2R_8$] —$CH_2CH_2CO_2R_8$ where $R_8$ is H or an alkyl containing 1 to 20 carbons. Particularly preferred compounds are where $R_5$ is —O— hexyl and $R_7$ is [—$CO_2H$] —$CH_2CH_2CO_2H$ or [—$CO_2CH_3$] —$CH_2CH_2CO_2CH_3$. The pyropheophorbides of the invention are combined with excipients to provide pharmaceutically acceptable formulations suitable for use in photodynamic therapy.

The invention also includes methods of synthesizing compounds of formula I and II.

The invention includes injectable pharmaceutical compositions containing the pyropheophorbide compounds of the invention as active ingredients and to methods of conducting photodynamic therapy using the compounds and compositions of the invention.

The invention also includes the pyropheophorbide compounds of the invention conjugated to a ligand which is capable of binding a specific receptor such as a cellular receptor, or an antibody which is capable of binding to a particular antigen and to compositions containing these conjugates and methods of conducting photodynamic therapy using the conjugates and their compositions.

A primary object of the invention is to provide pyropheophorbide compounds, pharmaceutical compositions containing such compound and method of treatment carried out using such compounds in a photodynamic therapy.

Other objects are to provide methods of treating humans with tumor cells which cells replicate abnormally fast, treating atherosclerosis or inactivating bacteria or virus infections.

A feature of the present invention is that the pyropheophorbide compounds of the invention absorb light further into the red portion of the spectrum as compared with conventional compounds used in photodynamic therapy.

An advantage of the present invention is that the pyropheophorbide compounds and pharmaceutical compositions of the invention optimize tissue penetration and are retained in the skin for relatively short periods of time as compared with other compounds used in photodynamic therapy.

Another advantage of the present invention is that the pyropheophorbide compounds of the invention have a greater toxicity with respect to tumor cells and diseased tissue as compared with the toxicity of conventional compounds used in photodynamic therapy.

Another advantage of the invention is that the pyropheophorbides can be synthesized as free acids (e.g. in formula I or II when $R_3$ or $R_7$ are —$CO_2H$) allowing ease in formulation without the need for liposomes or detergents.

Another advantage of the invention is the pyropheophorbide of the invention are active at very low doses of injected material as compared to conventional photosensitizers used in photodynamic therapy.

These and other objects, advantages and features of the present invention will become apparent to those persons skilled in the art upon reading the details of the structure, synthesis and usage as more fully set forth below, reference being made to the accompanying structural formula forming a part herein wherein like symbols refer to like molecular moieties throughout.

DETAILED DESCRIPTION OF PREFERRED EMBODIMENTS OF THE INVENTION

Figure 1:
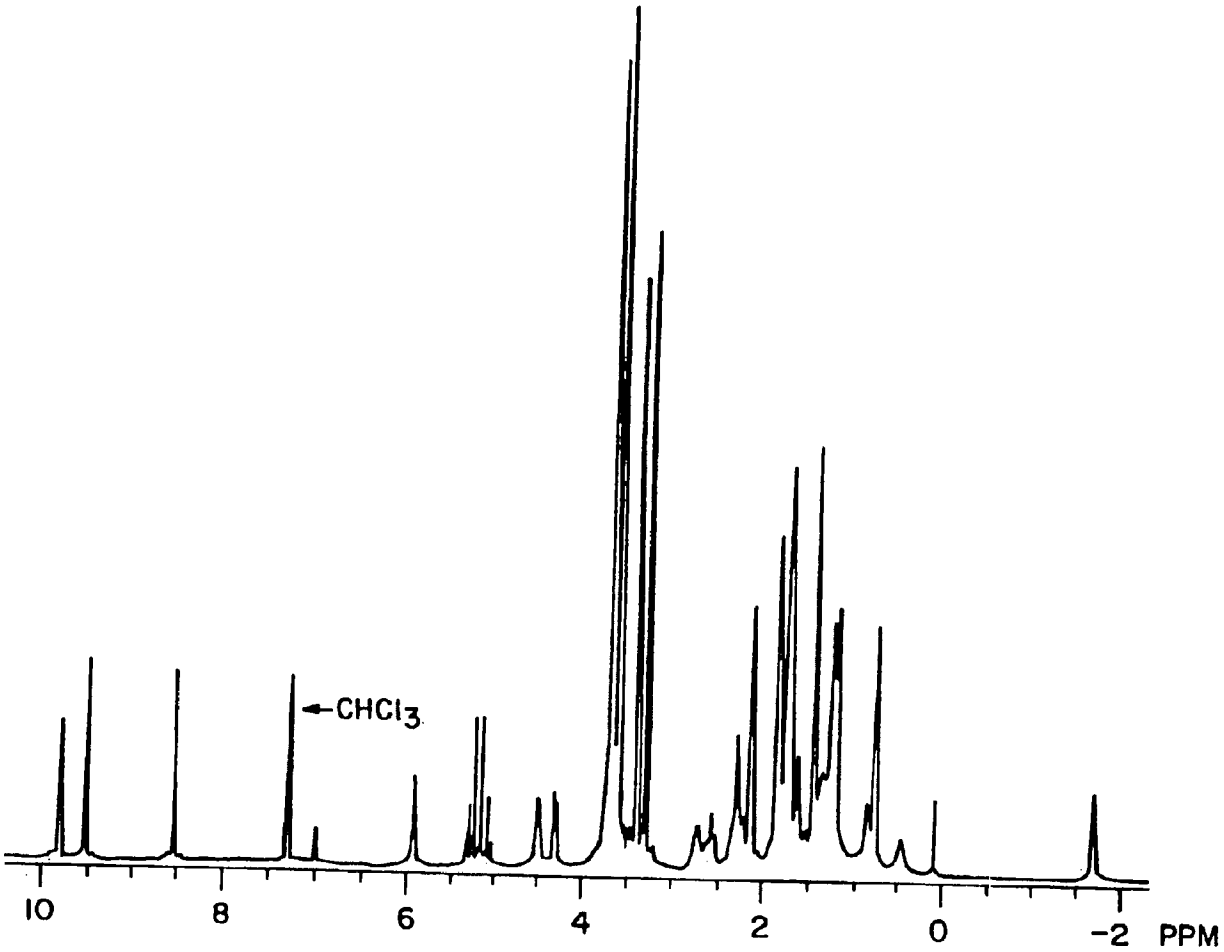
FIG. 1 is a FAB mass spectrum of the compound of formula II(a).

Before the present pyropheophorbide compounds, pharmaceutical compositions, methods of synthesizing and using such compounds are disclosed, it is to be understood that this invention is not limited to the particular compounds, compositions, methods of use or synthesis as described as such may, of course, vary. It is also to be understood that the terminology used herein is for the purpose of describing particular embodiments only, and is not intended to be limiting since the scope of the present invention will be limited only by the appended claims.

It is to be noted that as used in this specification and the appended claims, the singular forms "a", "and" and "the" include plural reference unless the context clearly dictates otherwise thus, for example, reference to "a pyropheophorbide" includes mixtures of such pyropheophorbides, reference to "an antibody" includes mixtures of such antibodies and reference to "the method of treatment" includes reference to like methods which will become apparent to those skilled in the art upon reading this disclosure.

Unless defined otherwise all technical and scientific terms used herein have the same meaning as commonly understood by one of ordinary skill in the art of photodynamic therapy. Although any methods and materials similar or equivalent to those described herein may be used in the practice or testing of the present invention, attempts have been made to describe preferred methods and materials below.

The essence of the invention is the disclosure of novel compounds and pharmaceutical compositions containing such compounds which have been found to be highly effective in the treatment of cancer when used in connection with a photodynamic therapy. More specifically, the compounds are pyropheophorbide compounds which are encompassed by the following general structural formulae I and II.

I

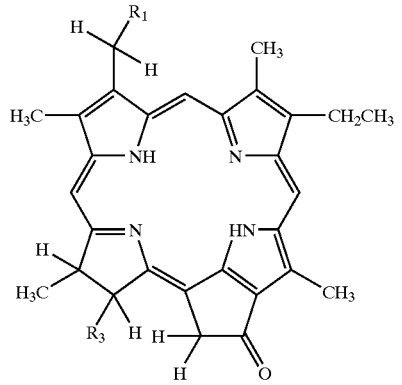

wherein $R_1$ is [$CH_2OR_2$] —$CH_2OR_2$ where $R_2$ is a primary or secondary alkyl containing 1 to 20 (preferably 5–20) carbons; and $R_3$ is [—$CO_2R_4$] —$CH_2CH_2CO_2R_4$ where $R_4$ is H or an alkyl containing 1 to 20 carbons. Preferred compounds are when $R_1$ is —$CH_2$—O—hexyl and $R_3$ is [—$CO_2CH_3$] —$CH_2CH_2CO_2CH_3$ or [—$CO_2H$] —$CH_2CH_2CO_2H$. Other compounds of the invention are encompassed by formula II as follows:

II

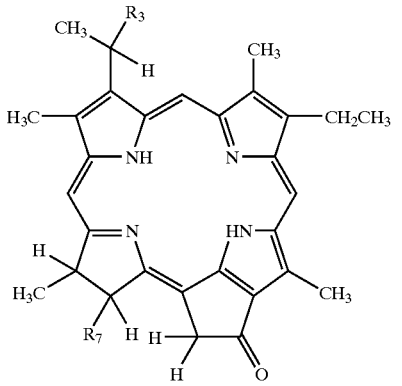

wherein $R_5$ is —$OR_6$ where $R_6$ is a primary or secondary alkyl containing 1 to 20 (preferably 5–20) carbons and $R_7$ is [—$CO_2R_8$] —$CH_2CH_2CO_2R_8$ where $R_8$ is H or an alkyl containing 1 to 20 carbons. Particularly preferred compounds are where $R_5$ is —O—hexyl and $R_7$ is [—$CO_2H$] —$CH_2CH_2CO_2H$ or [—$CO_2H_3$] —$CH_2CH_2CO_2CH_3$.

The pyropheophorbide compounds of structural formulae I and II can be formulated into pharmaceutical compositions and administered to patients in therapeutically effective amounts in order to treat cancer.

Although the invention encompasses all of the compounds of structural formulae I and II it has been found that the compound of structural formula IIa is particularly effective in the treatment of cancer when used in connection with photodynamic therapy. Structural formula IIa is put forth below:

[

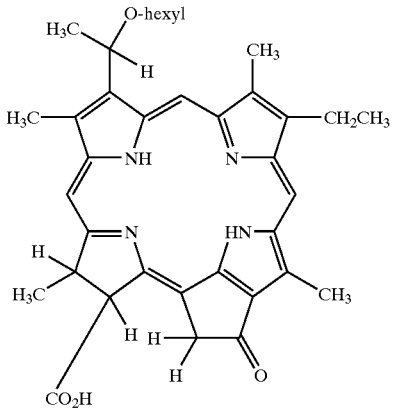

]

-continued

IIa

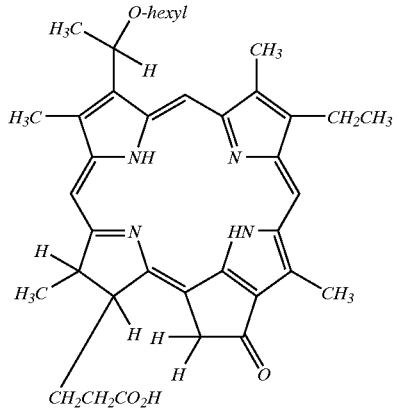

A generalized reaction scheme for the synthesis of the compound of structural formula IIa is put forth below:

Scheme 1

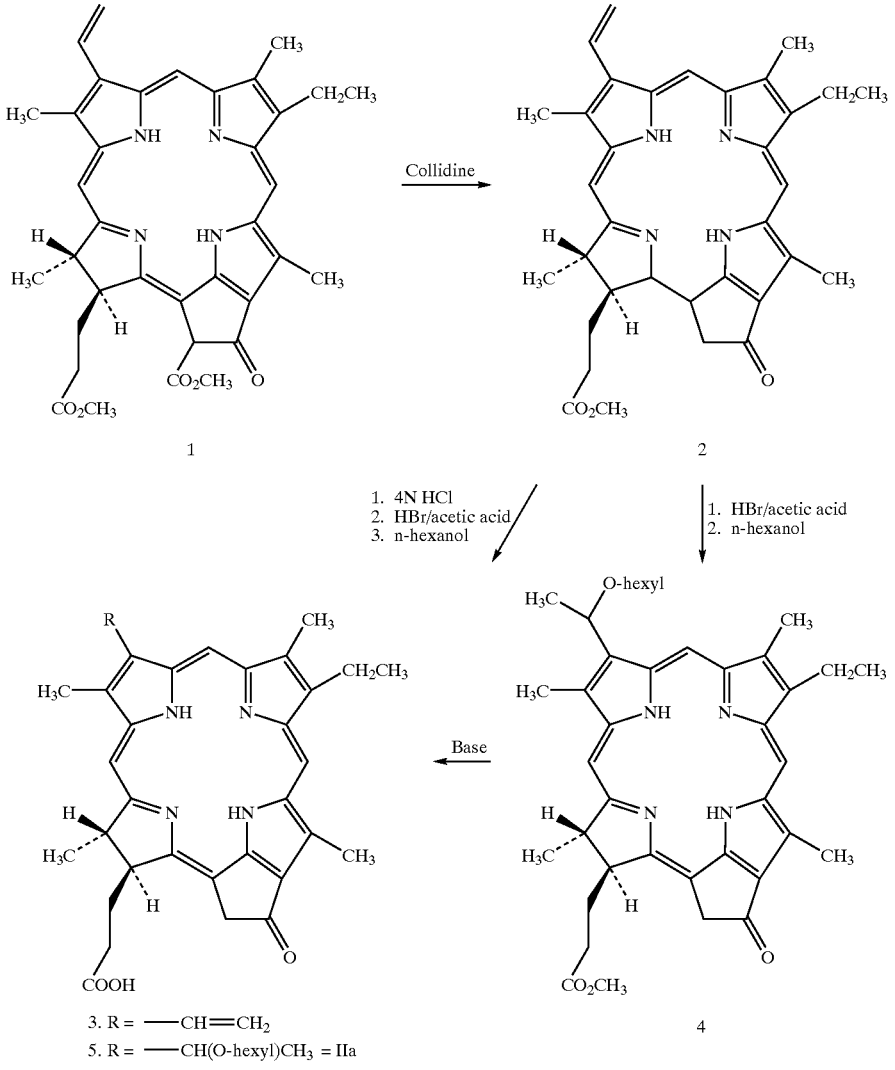

STARTING MATERIALS

The starting material for preparation of the red light-absorbing compounds is methyl pheophorbide-a, which is isolated from Spirulina destridratada by the method of Smith and Goff (D. Goff, Ph.D. Thesis, Univ. of Calif., Davis, Calif. 95616, 1984 incorporated herein by reference). Briefly, 500 gm dried Spirulina was slurried in a large volume of acetone and then liquid nitrogen was added to form a frozen slush. The slush was transferred to a 3-necked, 5-liter round bottom flask and heated to reflux under nitrogen with stirring for 2 hours. The mixture was filtered through Whatman paper on a Buchner funnel with extensive acetone washing. The extraction and filtration process was repeated 2 more times; all green color could not be removed from the solid.

The green filtrate was evaporated and purified by flash chromatography on Grade V neutral Alumina, eluting first with n-hexane to remove a fast running yellow band and then with dichloromethane to obtain the major blue/gray peak containing pheophytin-a. Treatment of pheophytin-a with 500 ml sulfuric acid in methanol for 12 hours at room temperature in the dark under nitrogen was followed by dilution with dichloromethane. The reaction mixture was rinsed with water and then 10% aqueous sodium bicarbonate and the organic layer was dried, evaporated, and the residue recrystallized from dichloromethane/methanol to obtain 1.8 gm methyl pheophorbide-a. Methyl pheophorbide-a appears to be inactive in the in vivo tumoricidal activity assay when injected at a dose of 5 mg/kg.

CONJUGATES AND LABELED PYROPHEOPHORBIDES

In addition to using compositions which consist essentially of the above-defined compounds or preparations as active ingredient, it is possible to use derivatized forms in order to provide a specific targeting mechanism. Commonly used target-specific components include monoclonal antibodies and ligands which bind to a cellular receptor. The compositions can also be conveniently labeled.

The target-specific component can then be, for example, an immunoglobulin or portion thereof or a ligand specific for a particular receptor. The immunoglobulin component can be any of a variety of materials. It may be derived from polyclonal or monoclonal antibody preparations and may contain whole antibodies or immunologically reactive fragments of these antibodies such as $F(ab')_2$, FAB, or FAB' fragments. Use of such immunologically reactive fragments as substitutes for whole antibodies is well known in the art. See, for example, Spiegelberg, H. L., in "Immunoassays in the Clinical Laboratory" (1978) 3:1–23 incorporated herein by reference.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L., supra.

Particularly useful antibodies include the monoclonal antibody preparation CAMAL1 which can be prepared as described By Malcolm, A., et al, Ex Hematol (1984) 12:539–547; polyclonal or monoclonal preparations of anti-M1 antibody as described by New, D., et al, J Immunol (1983) 130:1473–1477 (supra) and B16G antibody which is prepared as described by Maier, T., et l, J Immunol (1983) 131:1843; Steele, J. K., et al, Cell Immunol (1984) 90:303 all of which publications are incorporated herein by reference.

The foregoing list is exemplary and certainly not limiting; once the target tissue is known, an antibody specific for this tissue may be prepared by conventional means. Therefore the invention is applicable to effecting toxicity against any desired target.

The ligand specific for receptor refers to a moiety which binds a receptor at cell surfaces, and thus contains contours and charge patterns which are complementary to those of the receptor. It is well understood that a wide variety of cell types have specific receptors designed to bind hormones, growth factors, or neurotransmitters. However, while these embodiments of ligands specific for receptor are known and understood, the phrase "ligand specific for receptor," as used herein, refers to any substance, natural or synthetic, which binds specifically to a receptor.

Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances which succeeds in binding to the receptor is also included.

The conjugation of the target-cell-specific component to the compounds of the invention can be as effected by any convenient means. For proteins, such as Ig and certain receptor ligands, a direct covalent bond between these moieties may be effected, for example, using a dehydrating agent such as a carbodiimide. A particularly preferred method of covalently binding the compounds of the invention to the immunoglobulin moiety is treatment with 1-ethyl-3-(3-dimethylamino propyl) carbodiimide (EDCI) in the presence of a reaction medium consisting essentially of dimethyl sulfoxide (DMSO).

Of course, other dehydrating agents such as dicyclohexylcarbodiimide or diethylcarbodiimide could also be used as well as conventional aqueous and partially aqueous media.

Nonprotein receptor ligands can be conjugated to be dimers and trimers according to their relevant functional groups by means known in the art.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Co. These linkers are either homo- or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate, to the target-specific component include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

The compounds of the invention per se or the conjugates may be further derivatized to a compound or ion which labels the drug. A wide variety of labeling moieties can be used, including radioisotopes and fluorescent labels. Radioisotope labeling is preferred, as it can be readily detected in vivo.

The compounds which are alone or are conjugates with a specific binding substance can be labeled with radioisotopes by coordination of a suitable radioactive cation in the porphyrin system. Useful cations include technetium and indium. In the conjugates, the specific binding substances can also be linked to label.

ADMINISTRATION AND USE

In general, the pyropheophorbide compounds of the invention are administered to a host such as a human suffering from cancer in therapeutically effective amounts by any suitable means such as injection which may be IV or IM or may be administered transdermally. The pyropheophorbide compounds of the invention accumulate in tumor cells to a much higher degree than they accumulate in surrounding normal tissues. After being provided with sufficient time so as to accumulate in the tumor tissue, the pyropheophorbide compounds are exposed to a particular wavelength of light which causes the compounds to become cytotoxic, thus destroying the tumor or diseased tissue which the pyropheophorbide compounds have accumulated in. This is accomplished without causing irreversible damage to surrounding normal tissues wherein there has not been an accumulation of the pyropheophorbide compounds.

The compounds and their conjugates with target-specific substances of the invention are useful, in general, in the manner known in the art for hematoporphyrin derivative and for Photofrin II compositions. These compositions are useful in sensitizing neoplastic cells or other abnormal tissue to destruction by irradiation using visible light—upon photoactivation, the compositions have no direct effect, nor are they entered into any biological event; however the energy of photoactivation is believed to be transferred to endogenous oxygen to convert it to singlet oxygen. This single oxygen is thought to be responsible for the cytotoxic effect. In addition, the photoactivated forms of porphyrin fluorescence which fluoresce can aid in localizing the tumor. Thus, the dimer and trimer compounds of the invention are not consumed or altered in exerting their biological effects.

Typical indications, known in the art, include destruction of tumor tissue in solid tumors, dissolution of plaques in blood vessels (see, e.g. U.S. Pat. No. 4,512,762); treatment of topical conditions such as acne, athlete's foot, warts, papilloma, and psoriasis and treatment of biological products (such as blood for transfusion) for infectious agents, since the presence of a membrane in such agents promotes the accumulation of the drug. Other uses include treating humans suffering from atherosclerosis and inactivating bacterial or viral infections.

The compositions are formulated into pharmaceutical compositions for administration to the subject or applied to an in vitro target using techniques known in the art generally. A summary of such pharmaceutical compositions may be found, for example, in Remington's Pharmaceutical Sciences, Mack Publishing Co., Easton, Pennsylvania, latest edition. The compositions, labeled or unlabeled, can be administered systemically, in particular by injection, or can be used topically.

Injection may be intravenous, subcutaneous, intramuscular, or even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic auxiliary substances such as wetting or emulsifying agents, pH buffering agents and so forth.

Systemic administration can also be implemented through implantation of a slow release or sustained release system, by suppository, or, if properly formulated, orally. Formulation for these modes of administration are well known in the art, and a summary of such methods may be found, for example, in Remington's Pharmaceutical Sciences (supra).

If the treatment is to be localized, such as for the treatment of superficial tumors or skin disorders, the compositions may be topically administered using standard topical compositions involving lotions, suspensions, or pastes.

The quantity of compound to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissue, such as those which comprise conjugates with a highly specific monoclonal immunoglobulin preparation or specific receptor ligand, dosages in the range of 0.05–1 mg/kg are suggested. For compositions which are less specific to the target tissue, larger doses, up to 1–10 mg/kg may be needed. The foregoing ranges are merely suggestive, as the number of variables in regard to an individual treatment regime is large and considerable excursions from these recommended values are expected. Further, because of slight solubility in water, certain compounds of the invention may be administered directly in saline or 5% glucose solution, thus avoiding the complications of detergents or other solubilizing agents.

Those skilled in the art of photodynamic therapy and compounds related to the present invention will be better able to determine an appropriate dosage and overall dosage regime when taking a number of factors into consideration. For example, the size, weight and condition of the patient must be considered as must be the responsiveness of the patient and their disease to the particular therapy. It is believed that even relatively small doses administered a single time can have a beneficial effect. Further, extremely large doses could, of course, be toxic. Accordingly, rather than providing specific information on dosage amount and intervals between dosing, attention should be paid to conventional factors used in determining such dosing while considering that the pyropheophorbide compounds of the invention have a greater degree of toxicity with respect to tumor cells and therefore can generally be administered in smaller amounts than the conventional compounds used in connection with photodynamic therapy.

EXAMPLES

The following examples are put forth so as to provide those of ordinary skill in the art with a complete disclosure and description of how to make the pyropheophorbide compounds and pharmaceutical compositions of the invention and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, temperature is in degrees Centigrade, and pressure is at or near atmospheric.

EXAMPLE 1

Methyl pyropheophorbide-a (2):

Methyl pheophorbide-a (1, 1.0 g) was obtained from alga Spirulina destridratada by following the procedure described in K. M. Smith, D. A. Goff and D. J. Simpson, J. An. Chem. Soc., 1986, 107, 4941–4954; and R. K. Pandey, D. A. Bellnier, K. M. Smith and T. J. Dougherty, Photochem. Photobiol., 1991, 53, 65–72, both of which are incorporated herein by reference. The methyl pheophorbide-a was heated under reflux in collidine (100 ml) for 90 min during slow passage of a stream of nitrogen. See G. W. Kenner, S. W. McCombie and K. M. Smith, J. Chem. Soc. Perkin Trans. 1973, 1, 2517–2523, incorporated herein by reference. The solution is evaporated (0.1 mm Hg) and the residue was recrystallized from dichloromethane/methanol. Yield 820 mg; 91%, m.p. 217°–219° C., lit. 220°–225° C.; H. Fisher and A. Stern, Die Chemie des Pyrrole, vol II, Part 2, pp. 64 and 74, Akademische Verlag, Leipzig incorporated herein by reference. Vis: (max) 410 (112 000); 508 (11 000); 536 (9 600); 610 (8 200); 666 (45 000); NMR, ppm; 9.50, 9.38, 8.52 (each s, 3H, 3 meso H); 7.95–8.05 (m, 1H, CH═$CH_2$); 6.30 and 6.15 (each s, 1H, CH—$CH_2$); 5.27 to 5.12 (q, 2H, 10—$CH_2$); 4.50 (m, 8-HO; 4.28 (m, 7-H); 3.70 (q, 2H, $CH_2CH_3$); 3.68 (s, 3H, $CHCHCO_2CH_3$); 3.62, 3.40, 3.22 (each s, 3H, $3CH_3$); 2.70 (7a-H); 2.31 (7a'-H); 2.56 (7b-H); 2.29 (7b'-H); 1.82 (d, 3H, 8-CH 1.70 (t, 3H, $CH_2CH_3$); 1.70 (s, 2H,2 NH)

Pyropheophorbide-a (3):

Methyl pyropheophorbide-a (2, 250 mg) was dissolved in distilled tetrahydrofuran (50 ml) and 4N HCl (125 ml) was added in one lot. The reaction mixture was stirred under nitrogen atmosphere at room temperature for 4 hours. The reaction was monitored by analytical tlc (silica plates), using 10% methanol/dichloromethane as a mobile phase. The reaction mixture was then poured in ice water, extracted with dichloromethane. The dichloromethane layer was washed several times with water (3×200 ml). The organic layer was separated and dried over anhydrous sodium sulfate. Evaporation of the solvent gave a residue, which was crystallized from dichloromethane/hexane. Yield, 225 mg. The purity of the compound was ascertained by tlc and the structure was confirmed by NMR spectroscopy. The NMR data were similar as described for 2 except the resonances for the —$OCH_3$ protons of the propionic ester (—$CH_2CH_2CO_2CH_3$) were missing.

Methyl-2-{1(O-hexyl)ethyl}-devinyl pyropheophorbide (4):

Pyropheophorbide-a (2, 200 mg) was dissolved in 30% HBr/acetic acid (5.0 ml) and the reaction mixture was stirred in a glass stoppered flash (rubber septum can also be used) at room temperature for 2.5 hours. The solvent was removed under high vacuum (1 mm Hg) and the resulting 1-bromo ethyl derivative was immediately treated with n-hexanol (3.0 ml) under nitrogen atmosphere. The reaction mixture was stirred at room temperature for 45 min, diluted with dichloromethane (100 ml). The dichloromethane layer was washed with water (3×200 ml) till the aqueous phase is neutral and then dried over anhydrous sodium sulfate. Evaporation of the solvent gave a residue, which was chromatographed over Alumina Grade III (6% water/neutral Alumina) and eluted with dichloromethane. The first fraction was a mixture of the starting material and the desired product (minor quantity). Further elution with same solvent gave the desired product. The appropriate eluates were combined. Evaporation of the solvent afforded a sticky solid, which can be crystallized from dichloromethane/hexane. Yield 70%. (see Scheme-1), Vis,(max); 408 (90 000); 471 (3 200), 506 (8600); 536 (8,500); 604 (7,250); 660 (41 500). NMR, ppm; 9.79, 9.51, 8.53 (each s, 1H, meso H); 5.90 (q, 2H, —CH (O-hexyl)$CH_3$; 5.08–5.30 (q, 2H, 10—$CH_2$); 4.47 (m, 8H); 4.29 (m, 7-HO; 3.75 (q, 2H, $CH_2CH_3$); 3.67 (s, 3H, $CH_2CH_2CO_2CH_3$); 3.67 (s, 6H, 2×$CH_3$); 3.38 and 3.27 (each s, $CH_3$); 2.68 (7a-H) 2.28 (7a'-H), 2.55 (7b-H); 2.20 (7b'-H); 1.80 (d, 3H, $CH_2CH_3$); −1.70 (s, 2H, 2 NH); for the hexyl group, 3.72 (t, 2H, O—$CH_2CH_2$); 1.73 (2H, $CH_2$); 1.25 [bs, merged, 6H, $(CH_2)_3$]; 0.78 (t, 3H, $CH_3$). (see FIG. 1).

2-{1(O-hexyl)ethyl}devinyl pyropheophorbide-a (5):

Pyropheophorbide-a (3, 200 mg) was reacted with 30% HBr/acetic acid and then with n-hexanol by following the method as discussed for 4 and the desired product was isolated in 60 to 65% yield. The structure was confirmed by NMR spectroscopy.

EXAMPLE 2

Tumor Treatment

When 2-[1-(O-hexyl)ethyl]devinyl pyropheophorbide-a - structure (5) in Scheme 1: S—RO—where R═$(CH_2)_5CH_3$ and m═H, (formula IIa) synthesized as indicated (5.0 mg) is dissolved in Tween 80 (0.1 ml) and mixed with 10 ml Hanks Balanced Salt Solution (HBSS), a solution of approximately 0.5 mg/ml in 0.1% Tween 80 is produced after filtration through a 0.22 AM Millipore filter. Ten DBA/2 mice with 0.4–0.5 mm diameter subcutaneous SMT-F tumors in the axilla are injected intravenously with 0.3 mg/kg body weight of the above solution (after dilution in HBSS so that the injected volume per mouse is approximately 0.2 ml). Approximately 24 h later the tumor area (having been shaved and depilated prior to tumor implant) is exposed to laser light at 660–670 nm for 30 min at a power of 75 mW/$cm^2$ to deliver 135 Joules/$cm^2$. Alternately, a Xenon arc lamp filtered to emit a broader band width near 670 nm and approximately 283 Joules/$cm^2$ can be used.

The day after light treatment all the tumors are seen to be flat (non-palpable) and slight skin blanching over the area is noted. This progresses to frank tumor necrosis over the next few days. At 7 days post treatment all tumors remain non-palpable and necrotic. At 30 days post treatment, six of the 10 tumors remain non-palpable, and one remains tumor-free to 90 days post treatment.

EXAMPLE 3

Skin Clearance

Six albino Swiss mice (HaICR) are injected intravenously with a dose of 0.1 mg/kg body weight of the compound of formula IIa prepared as in Example 1. After approximately 24 h, the hind foot of the animal is exposed to the same dose of either laser light at 660–670 nm (135 Joules/$cm^2$) or the Xenon arc lamp (283 Joules/$cm^2$) as above. The reaction of the foot is scored for damage over the next few days to determine the maximum effect, which in this case is a value 0.3 equivalent to slight edema. If the internal between the injection and light treatment is extended to approximately 48 h, the foot reaction is zero (no damage incurred), indicating either clearance or metabolism of the sensitizer.

Data obtained as a result of experiment carried out is put forth below in Table 1.

TABLE 1

In Vivo Tumor Photosensitizing Activity of Pyropheophorbide Ethers[1]

| Injected Dose (mg/kg) | Time Interval (hours) | Wavelength | Tumor Response[2] Day 1 | Day 7 | Day 30 | Day 90 | Normal Foot Response[3] Time Interval (hours) | Maximum Reaction |
|---|---|---|---|---|---|---|---|---|
| Formula II $R_5$ = —O—$(CH_2)_5CH_3$ $R_7$ = —$CO_2H$ | | | | | | | | |
| 0.05 | 24 | 659 | 0/40 | — | — | — | | |
| 0.1 | 24 | 659 | 6/6 | 6/6 | 1/6 | 1/6 | 24 | 0.3 |
| 0.3 | 24 | 659 | 5/5 | 4/5 | 0/5 | — | 48–72 | 0 |
| 0.3 | 24 | 655 | 0/10 | — | — | — | — | — |
| 0.3 | 24 | 665 | 10/10 | 10/10 | 2/10 | 0/10 | — | — |
| 0.3 | 24 | 670 | 10/10 | 10/10 | 6/10 | 1/10 | — | — |
| 0.3 | 24 | 680 | 1/10 | 0/10 | — | — | — | — |
| Formula II $R_5$ = —O—$(CH_2)_5CH_3$ $R_7$ = —$CO_2CH_3$ | | | | | | | | |
| 0.3 | 24 | 660 | 6/6 | 6/6 | 3/6 | 3/6 | — | — |
| 0.1 | 24/660 | 5/5 | 3.5 | 0/5 | — | — | — | |
| Formula II $R_{20}$ = —O—$CH_3$ $R_7$ = —$CO_2CH_3$ | | | | | | | | |
| 0.1 | 24 | 660 | 0/6 | — | — | — | — | — |
| 0.5 | 3 | 660 | 0/6 | — | — | — | — | — |
| Formula I $R_1$ = —$CH_2O(CH_2)_5CH_3$ $R_1$ = —$CO_2CH_3$ | | | | | | | | |
| 0.3 | 24 | 660 | 6/6 | 2/6 | 0/6 | — | — | — |

[1]SMT-F tumor in DBA/2 mice; 135 J/cm$^2$ light from laser at 75 mW/cm$^2$
[2]Number of non-palpable tumors/Number treated tumors post light treatment on Day indicated
[3]White Albino Swiss mice; foot exposed using same conditions as for tumor treatment. Score of 0.3 - slight edema; 0 - no reaction.

The data put forth in Table 1 clearly demonstrates that the pyropheophorbide compounds of the invention are activated by light having a wavelength of about 660 nm. Further, when the compound were administered by injection and subjected to light having a wavelength of about 660 nm, the treatment was found to be highly effective with respect to reducing tumor size in as little as seven days.

Further, the data of Table 1 show compounds of the invention clear skin over a period of 24–48 hours after administration. This is a desirable feature in that the patient is not subjected to prolonged cutaneous photosensitivity. The data of Table 1 also show that the hexyl ethers of formula II are preferred over methyl ethers in terms of effecting tumor growth when used in photodynamic therapy.

While the present invention has been described with reference to specific compounds, formulations and methods, it is to be understood by those skilled in the art that various changes maybe made and equivalents may be substituted without departing from the true spirit and scope of the invention. In addition, many modifications may be made to adapt to a particular individual, method of administration, process of synthesizing, etc., which are within the scope of the present invention. All such modifications are intended to be within the scope of the claims appended hereto.

We claim:

1. A conjugate comprising a target-specific component covalently bound to a compound of formula I:

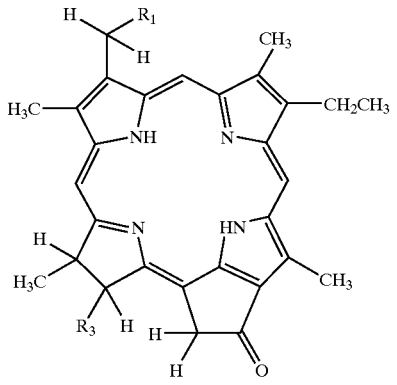

wherein $R_1$ is $CH_2OR_2$ where $R_2$ is a primary or secondary alkyl containing 1 to 20 carbons; and $R_3$ is [—$CO_2R_4$] —$CH_2CH_2CO_2R_4$ where $R_4$ is H or an alkyl containing 1 to 20 carbons.

2. The conjugate of claim 1, wherein the target-specific component is selected from the group consisting of a ligand capable of binding to a specific cellular receptor, and an antibody capable of binding to a particular antigen.

3. The conjugate of claim 2, wherein the antibody is a monoclonal antibody.

4. The conjugate of claim 2, wherein the ligand is selected from the group consisting of steroid hormones, and growth factors.

5. The conjugate of claim 2, wherein the conjugate is further attached to a detectable label.

6. The conjugate as claimed in claim 1, wherein $R_1$ is $CH_2$—O—Hexyl, $R_2$ is —$CH_3$, and $R_3$ is —$CO_2CH_3$.

7. A method to effect the destruction of a target virus, cell or tissue, comprising:

contacting said target with an effective amount of the conjugate of claim 1; and irradiating with light absorbed by said conjugate.

8. A pharmaceutical composition useful in treatment of a target virus, cells or tissue, comprising:

an effective amount of the conjugate of claim 1 in admixture with a pharmaceutically acceptable excipient.

9. A conjugate comprising a target-specific component covalently bound to a compound of formula II:

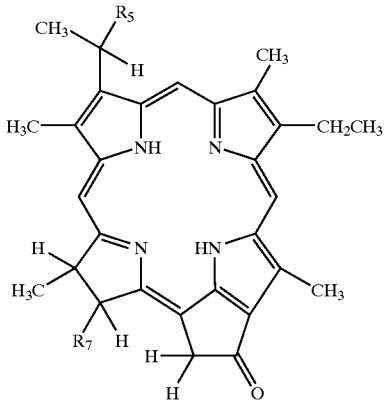

wherein $R_5$ is —$OR_6$ where $R_6$ is a primary or secondary alkyl containing 1 to 20 carbons and $R_7$ is [—$CO_2R_8$] —$CH_2CH_2CO_2R_8$ where $R_8$ is H or an alkyl containing 1 to 20 carbons.

10. The conjugate of claim 9, wherein the target-specific component is selected from the group consisting of a ligand capable of binding to a specific cellular receptor, and an antibody capable of binding to a particular antigen.

11. The conjugate of claim 10, wherein the antibody is a monoclonal antibody.

12. The conjugate of claim 10, wherein the ligand is selected from the group consisting of steroid hormones, and growth factors.

13. The conjugate of claim 10, wherein the conjugate is further attached to a detectable label.

14. The compound as claimed in claim 9, wherein $R_5$ is —O—hexyl and $R_7$ is —$CO_2CH_3$.

15. The compound as claimed in claim 9, wherein $R_5$ is —O—$(CH_2)_5CH_3$ and $R_7$ is selected from the group consisting of $CO_2CH_3$ and —$CO_2H$.

16. A method to effect the destruction of target virus, cells or tissue, comprising:

contacting said target with an effective amount of the conjugate of claim 9; and irradiating with light absorbed by said conjugate.

17. A pharmaceutical composition useful in treatment of a target virus, cells or tissue, comprising:

an effective amount of the compound of claim 9 in admixture with a pharmaceutically acceptable excipient.

18. A method of treating a human with abnormal cells which replicate at an abnormally high rate, comprising the steps of:

administering to the human therapeutically effective amount of a conjugate comprising a target-specific component covalently bound to a compound of formula II

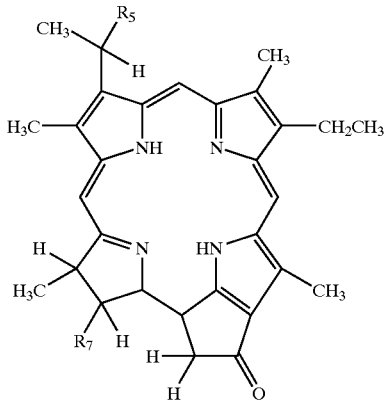

wherein $R_5$ is —$OR_6$ where $R_6$ is a primary or secondary alkyl containing 5 to 20 carbons and $R_7$ is [—$CO_2R_8$] —$CH_2CH_2CO_2R_8$ where $R_8$ is H or —$CH_3$;

allowing the conjugate to accumulate on the abnormal cells; and irradiating the conjugate with a wavelength of light which is absorbed by the compound of formula II and thereby generating a cytotoxic effect with respect to the abnormal cells, wherein the conjugate is administered in an amount in the range of 0.01 mg/kg to 1.0 mg/kg of body weight.

19. The method as claimed in claim 18 wherein the conjugate is administered at timed intervals in the range of from every 3 hours to every 72 hours for over a period of from 1 day to 30 days and wherein the wavelength of the light is in the range of 600 to 700 nm.

20. The method as claimed in claim 18, wherein $R_5$ is —O—hexyl and $R_7$ is —$CO_2H$ and wherein the wavelength of the light is about 660 nm.

* * * * *